United States Patent [19]

Mummey

[11] Patent Number: 4,855,459

[45] Date of Patent: Aug. 8, 1989

[54] PROCESS FOR THE PRODUCTION OF MALEIC ANHYDRIDE

[75] Inventor: Michael J. Mummey, Foley, Mo.

[73] Assignee: Monsanto Company, St. Louis, Mo.

[21] Appl. No.: 145,795

[22] Filed: Jan. 19, 1988

[51] Int. Cl.$^4$ .......................................... C07D 307/60
[52] U.S. Cl. ................... 549/260; 549/259
[58] Field of Search ............... 549/259, 260

[56] References Cited

U.S. PATENT DOCUMENTS

| | | | |
|---|---|---|---|
| 3,856,824 | 12/1974 | Raffelson et al. | 260/346.8 A |
| 3,862,146 | 1/1975 | Boghosian | 260/346.8 A |
| 3,864,280 | 2/1975 | Schneider | 252/435 |
| 3,888,886 | 6/1975 | Young et al. | 502/209 X |
| 3,899,516 | 8/1975 | Dickason | 260/346.8 A |
| 3,904,652 | 9/1975 | Frank | 260/346.3 |
| 3,980,585 | 9/1976 | Kerr et al. | 252/437 |
| 4,002,650 | 1/1977 | Bremer et al. | 260/346.8 A |
| 4,018,709 | 4/1977 | Barone et al. | 252/435 |
| 4,187,235 | 9/1979 | Katsumoto | 260/346.75 |
| 4,251,390 | 6/1979 | Barone | 252/435 |
| 4,294,722 | 10/1981 | Bremer et al. | 252/435 |
| 4,312,787 | 12/1979 | Dolhyj | 252/435 |
| 4,315,864 | 2/1982 | Bremer et al. | 260/346.75 |
| 4,333,853 | 6/1982 | Milberger et al. | 252/435 |
| 4,342,699 | 8/1982 | Palmer et al. | 549/259 |
| 4,501,907 | 2/1985 | Kwentus et al. | 549/259 |
| 4,562,268 | 12/1985 | Wrobleski et al. | 549/259 |
| 4,632,915 | 12/1986 | Keppel et al. | 502/209 |
| 4,701,433 | 10/1987 | Edwards | 549/259 |

FOREIGN PATENT DOCUMENTS 98039 8/1983 European Pat. Off. .

Primary Examiner—Mary C. Lee
Assistant Examiner—Bernard I. Dentz
Attorney, Agent, or Firm—Wendell W. Brooks

[57] ABSTRACT

Maleic anhydride is produced by the catalytic vapor phase partial oxidation of a nonaromatic hydrocarbon having at least four carbon atoms in a straight chain with molecular oxygen or a molecular oxygen-containing gas in the presence of phosphorus-vanadium mixed oxide oxidation catalyst. The catalyst is diluted with an inert solid material in an amount sufficient to form a catalyst-inert solid material composition effective to stabilize the maleic anhydride yield such that the average yield decay is less than 0.30% of the established initial maleic anhydride yield per month over an extended period of sustained operations.

34 Claims, No Drawings

PROCESS FOR THE PRODUCTION OF MALEIC ANHYDRIDE

BACKGROUND OF THE INVENTION

1. Field of the Invention

This invention relates to a process for the production of maleic anhydride by the oxidation of nonaromatic hydrocarbons. More particularly, this invention relates to an improved process for the partial oxidation of nonaromatic hydrocarbons in the vapor phase with molecular oxygen or a molecular oxygen-containing gas to maleic anhydride in excellent yields in a heat transfer medium-cooled fixed bed tube-type reaction zone containing a fixed bed of a phosphorus-vanadium mixed oxide oxidation catalyst diluted with an inert solid material in an amount sufficient to form a catalyst-inert solid material composition effective to stabilize the maleic anhydride yield such that the established initial maleic anhydride yield is substantially maintained over an extended period of sustained operations.

Maleic anhydride is of significant commercial interest throughout the world. It is used alone or in combination with other acids in the manufacture of alkyd and polyester resins. It is also a versatile intermediate for chemical synthesis. Significant quantities of maleic anhydride are produced each year to satisfy these varied needs.

2. Description of the Prior Art

Numerous catalysts containing mixed oxides of phosphorus and vanadium are disclosed in the prior art as being useful for the conversion of various organic feedstocks to maleic anhydride, and further that such catalysts wherein the valence of the vanadium is between about +3.8 and +4.8 are particularly well-suited for the production of maleic anhydride from saturated hydrocarbons having at least four carbon atoms in a straight chain. In many instances, such catalysts also contain added promoter elements which are considered to exist in the catalysts as the oxide. Common organic feedstocks include nonaromatic hydrocarbons such as n-butane, 1- and 2-butenes, 1,3-butadiene, or mixtures thereof.

U.S. Pat. No. 4,632,915 discloses catalysts comprising phosphorus, vanadium and oxygen, and a promoter component containing each of iron and lithium which are useful for the partial oxidation of nonaromatic hydrocarbons, particularly n-butane, with molecular oxygen or a molecular oxygen-containing gas in the vapor phase to produce maleic anhydride in excellent yields.

U.S. Pat. No. 4,562,268 relates to a process for the production of maleic anhydride from nonaromatic hydrocarbons in the presence of a phosphorusvanadium mixed oxide oxidation catalyst wherein the catalyst exhibits a single pass weight/weight productivity of at least 70 grams of maleic anhydride per kilogram of catalyst per hour.

U.S. Pat. No. 4,333,853 discloses a phosphorus-vanadium mixed oxide catalyst prepared by reducing vanadium substantially in the pentavalent valence state to a tetravalent valence state in the presence of a phosphorus-containing compound and in the absence of a corrosive reducing agent in an organic liquid medium capable of reducing the vanadium to a valence state less than +5, recovering the resulting vanadium-phosphorus mixed oxide catalyst precursor, drying such precursor, and calcining the precursor to obtain the active catalyst. Such catalysts reportedly are effective in the oxidation of C$_4$ hydrocarbons such as n-butane, 1- and 2-butenes, 1,3-butadiene, or mixtures thereof to produce maleic anhydride with selectivities ranging from 58.7% to 68 1% and yields (mole %) ranging from 51.4% to 59.5%.

U.S. Pat. No. 4,315,864 relates to a process for the production of maleic anhydride from normal C$_4$ hydrocarbons in the presence of a phosphorus-vanadium mixed oxide catalyst. The catalyst is prepared by reducing a pentavalent vanadium-containing compound in an olefinic, oxygenated organic liquid medium to a +4 valence in the absence of a corrosive reducing agent, recovering the resultant catalyst precursor, drying the catalyst precursor, and calcining the precursor to obtain the active catalyst.

U.S. Pat. No. 4,312,787 describes a catalyst which comprises an inert support and a catalytically active mixed oxide material coating of phosphorus and vanadium or of phosphorus, vanadium, and uranium on the outer surface of the support in an amount greater than 50% to about 80% by weight of the combined support and oxide material. Catalysts within the scope of the claims of the patent were reported to produce maleic anhydride from n-butane in yields ranging from 53% to 62.5%, with selectivities ranging from 57.4% to 67.9%.

U.S. Pat. No. 4,294,722 discloses a process for preparing catalysts containing mixed oxides of phosphorus and vanadium. In this process, a pentavalent vanadium-containing compound is reduced (at least in part) to a +4 valent state in an organic liquid medium in which the vanadium compound is at least partially soluble to form a solution or mixture. Any unsolubilized vanadium-containing compound having a particle size greater than 0.1 mm diameter is removed. The resulting solution is mixed with a pentavalent phosphorus-containing compound to form a precipitate which is recovered, dried, and calcined. Such catalysts are reported to be effective in the oxidation of nonbranched C$_4$ hydrocarbons, such as n-butane, 1- and 2-butenes, 1,3-butadiene, and mixtures thereof, in the presence of molecular oxygen or a molecular oxygen-containing gas in the vapor phase to maleic anhydride with good selectivity.

In U.S. Pat. No. 4,251,390, a zinc-promoted phosphorus-vanadium-oxygen catalyst is disclosed and claimed. The catalyst is prepared by reducing pentavalent vanadium in a substantially anhydrous organic medium to a lower valent state and digesting the reduced vanadium in the presence of a zinc promoter compound. The resulting catalyst is activated by bringing the catalyst to operating temperatures for the oxidation of n-butane to maleic anhydride at a rate of 5° C. to 10° C. per hour in the presence of a butane-in-air mixture.

In U.S. Pat. No. 4,187,235, a process is described for preparing maleic anhydride from n-butane in the presence of a phosphorus-vanadium-oxygen high surface area catalyst, that is, 10 to 100 square meters per gram (BET method). The catalyst is prepared by reducing pentavalent vanadium to a valence between +4.0 and +4.6 with a substantially anhydrous primary or secondary alcohol and contacting the reduced vanadium with phosphoric acid, followed by recovering and calcining the resultant vanadium (IV) phosphate compound.

U.S. Pat. No. 4,018,709 discloses a process for the vapor phase oxidation of normal C$_4$ hydrocarbons using catalysts containing vanadium, phosphorus, uranium, or tungsten or a mixture of elements from zinc, chromium, uranium, tungsten, cadmium, nickel, boron, and silicon.

In a preferred embodiment, the catalyst also contains an alkali metal or an alkaline earth metal, especially lithium, sodium, magnesium, or barium as active components. Typically, such catalysts are prepared in concentrated (37%) hydrochloric acid.

U.S. Pat. No. 4,002,650 discloses a process for the oxidation of n-butane used in a catalyst of the formula:

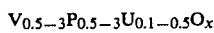

wherein x is a number taken to satisfy the valence requirements of the other elements present. In preferred preparative procedure, a mixture of vanadium pentoxide, concentrated hydrochloric acid, and uranyl acetate is heated under reflux. To this refluxing mixture is added 85% phosphoric acid. The resulting mixture is evaporated at atmospheric pressure and dried at 110° C., ground and screened to a suitable particle size, and activated by heating in an air flow at 482° C. for 16 hours.

In U.S. Pat. No. 3,980,585, a process is disclosed for the preparation of maleic anhydride from normal $C_4$ hydrocarbons in the presence of a catalyst containing vanadium, phosphorus, copper, oxygen, tellurium, or a mixture of tellurium and hafnium or uranium or a catalyst containing vanadium, phosphorus, copper, and at least one element selected from the group of tellurium, zirconium, nickel, cerium, tungsten, palladium, silver, manganese, chromium, zinc, molybdenum, rhenium, samarium, lanthanum, hafnium, tantalum, thorium, cobalt, uranium, and tin, optionally (and preferably) with an element from Groups 1a (alkali metals) or 2a (alkaline earth metals).

U.S. Pat. No. 3,888,866, discloses a process for the oxidation of n-butane by contacting the n-butane at a temperature from about 300° C. to about 600° C. with a phosphorus-vanadium-oxygen catalyst having a phosphorus/vanadium atom ratio of 0.5-2, promoted or modified with chromium, iron, hafnium, zirconium, lanthanum, and cerium, the promoter metal/vanadium atom ratio being between about 0.0025 and about 1. The catalysts are prepared by refluxing a reaction mixture of vanadium oxide, phosphoric acid, a hydrogen halide (usually hydrochloric acid), and a specified promoter metal-containing compound. The resulting catalyst precursors are recovered, dried, formed into structures, and calcined to produce the active catalyst.

U.S. Pat. No. 3,864,280, discloses phosphorus-vanadium mixed oxide catalyst having an intrinsic surface area from about 7 to about 50 square meters per gram. The catalysts are prepared by precipitation of a phosphorus-vanadium-oxygen complex from an essentially organic solvent medium in the absence of gross amounts of water. The resulting crystalline precipitate is activated by heating in air followed by a 1.5 mole % butane-in-air mixture, both at elevated temperatures.

U.S. Pat. No. 3,862,146, discloses a process for the oxidation of n-butane to maleic anhydride in the presence of a phosphorus-vanadium-oxygen catalyst complex, promoted or activated with a zinc, bismuth, copper, or lithium activator. The phosphorus/vanadium and activator/vanadium atom ratios are from about 0.5-5 and from about 0.05-0.5, respectively.

U.S. Pat. No. 3,856,824, discloses a process for the production of maleic anhydride by oxidation of saturated aliphatic hydrocarbons in the presence of a catalyst comprising phosphorus, vanadium, iron, oxygen, and added modifier comprising chromium combined with at least one element selected from the group consisting of nickel, boron, silver, cadmium, and barium.

European Patent Application No. 98,039 discloses a process for the preparation of phosphorus-vanadium mixed oxide catalysts, optionally containing an added promoter element selected from the group consisting of Group 1a (alkali metals), Group 2a (alkaline earth metals), titanium, chromium, tungsten, niobium, tantalum, manganese, thorium, uranium, cobalt, molybdenum, iron, zinc, hafnium, zirconium, nickel, copper, arsenic, antimony, tellurium, bismuth, tin, germanium, cadmium, and lanthanides, and mixtures thereof. The catalysts, which exhibit a phosphorus/vanadium atom ratio from about 0.8 to about 1.3 and a promoter/vanadium atom ratio from 0.01 to 0.5, are prepared in organic liquid reaction medium capable of reducing the vanadium to a valent state of approximately +4 to form a nonsolublized catalyst precursor, contacting the nonsolubilized catalyst precursor containing organic liquid with water to form a two-phase system having an upper organic liquid phase and a lower nonsolublized catalyst precursor-containing aqueous phase, drying the catalyst precursor, and calcining. The catalysts so obtained reportedly are useful in the production of maleic anhydride from normal $C_4$ hydrocarbons.

In general, the use of catalysts described in the prior art for the vapor phase partial oxidation of nonaromatic hydrocarbons to maleic anhydride involves passing a gaseous feed comprising the nonaromatic hydrocarbon and a molecular oxygen-containing gas—n-butane and air, for example—over a fixed bed of the oxidation catalyst in one or more heat transfer medium-cooled fixed bed tube-type reactors at temperatures of about 300° C. to about 600° C. The resulting effluent, containing maleic anhydride, by-product oxygenated hydrocarbons, unreacted nonaromatic hydrocarbon and oxygen, and inert gases is withdrawn from the reaction zone and maleic anhydride is substantially separated therefrom.

In an attempt to improve productivity in nonaromatic hydrocarbon, typically, n-butane, consumption, it has been proposed to employ oxidation feeds containing higher concentrations of the hydrocarbon than are typically employed in conventional operations and/or to recycle reaction zone effluent following separation of a major portion of the maleic anhydride product. For example, U.S. Pat. No. 4,342,699 discloses a vapor phase oxidation process for the production of maleic anhydride from n-butane wherein a butane concentration in the feed stream ranging from about 2 mole % to about 10 mole % is employed. In addition, a suitable catalyst, including phosphorus-vanadium-oxygen catalyst, is employed. Such catalyst is graded in activity along at least a portion of the length of the reaction zone, the lowest activity being at the feed end and the highest activity being at the exit end. Low conversion rates on the order of about 15–70% are attained, thereby necessitating recycling to the reaction zone a major portion of the effluent remaining following recovery of the maleic anhydride.

U.S. Pat. No. 3,899,516 discloses that space time yields and catalyst selectivity to maleic anhydride can be improved through the use of a feed containing n-butane and substantially pure (at least 95%) molecular oxygen in a mole ratio of at least 1:4, that is, at least 20 mole % n-butane and less than 80 mole % molecular oxygen in the feed.

U.S. Pat. No. 3,904,652 discloses the use of feeds containing greater than 1.7 mole percent n-butane, 3–13 mole % molecular oxygen, and 70–95 mole % inert gas, preferably nitrogen, in conjunction with 30% to 70% per pass conversion of n-butane and recycle of reaction effluent after separation of maleic anhydride in order to attain improved selectivity to maleic anhydride and ultimate conversion of n-butane.

In U.S. Pat. No. 4,501,907, a process is described wherein a feed concentration of from about 3 mole % to about 5 mole % n-butane-in-air at space velocities of from about 364 $hr^{-1}$ to about 536 $hr^{-1}$ are employed.

Although these prior art processes and catalysts generally produce the desired maleic anhydride product, the commercial utility of a catalyst system and a catalytic process is highly dependent upon the cost of the catalyst employed, the conversion of the reactants, the yield of the desired product(s), and the ability of the catalyst to maintain initially achieved yields of the desired product(s) over an extended period of operations without experiencing substantial yield decay, or stated differently, the actual productivity of the catalyst system over an extended period of sustained operations. In many instances, a reduction in the cost of a catalyst system employed in a given process on the order of a few cents per kilogram or pound, a small percent increase in the yield of a desired product, relative to the amount of catalyst required, and/or a decrease in product yield decay over extended periods of sustained operations represent a tremendous commercial economical savings and advantage. Accordingly, research efforts are continually being made to define new or improved catalyst systems and methods and processes of making new and old catalyst systems to reduce the cost and/or upgrade the activity, selectivity, and/or productivity, and extend the useful life of such catalyst systems in such processes. The discovery of the process of the instant invention, therefore, is believed to be a decided advance in the art.

SUMMARY OF THE INVENTION

This invention is directed to a process for minimizing maleic anhydride yield decay over extended periods of sustained operations. Accordingly, the primary object of this invention is to provide a process for stabilizing maleic anhydride yields at an established initial value over an extended period of sustained operations.

This and other objects, aspects, and advantages of the instant invention will become apparent to those skilled in the art from the accompanying description and claims.

The above objects are achieved by the improved process disclosed herein for the production of maleic anhydride by the catalytic vapor phase partial oxidation of nonaromatic hydrocarbons having at least four carbon atoms in a straight chain with molecular oxygen or a molecular oxygen-containing gas in the presence of a phosphorus-vanadium mixed oxide oxidation catalyst having a phosphorus/vanadium atom ratio of about 0.5 to about 2.0 the oxidation being conducted in a heat transfer medium-cooled fixed bed tube-type reaction zone packed with the catalyst under conditions sufficient to provide a single pass conversion of at least 70% of the hydrocarbon fed to the reaction zone and establish an initial maleic anhydride yield, the improvement comprising diluting the catalyst with an inert solid material in an amount sufficient to form a catalyst-inert solid material composition effective to stabilize the maleic anhydride yield such that average yield decay is less than 0.30% of the established initial maleic anhydride yield per month over an extended period of sustained operations.

DESCRIPTION OF THE PREFERRED EMBODIMENTS

In accordance with this invention, a process is provided for the production of maleic anhydride by the catalytic vapor phase partial oxidation of nonaromatic hydrocarbons having at least four carbon atoms in a straight chain with molecular oxygen or a molecular oxygen-containing gas in the presence of a phosphorus-vanadium mixed oxide oxidation catalyst having a phosphorus/vanadium (P/V) atom ratio of from about 0.5 to about 2.0, preferably from about 0.95 to about 1.2, the oxidation being conducted in a heat transfer medium-cooled fixed bed tube-type reaction zone packed with the catalyst under conditions sufficient to provide a single pass conversion of at least 70% of the hydrocarbon fed to the reaction zone and establish an initial maleic anhydride yield, the improvement comprising diluting the catalyst with an inert solid material in an amount sufficient to form a catalyst-inert solid material composition effective to stabilize the maleic anhydride yield such that average yield decay is less than 0.30%, preferably less than 0.25%, of the established initial maleic anhydride yield per month over an extended period of sustained operations.

It will be apparent to those skilled in the art that the length or duration of the extended period of sustained operations is not critical. All that is necessary is that such time period is of a duration sufficient to (a) achieve a substantially accurate determination of the maleic anhydride yield decay value and (b) make practicable the determination of the maleic anhydride yield decay. In general, a convenient duration for the extended period of sustained operations is at least six (6) months.

For purposes of this invention, the term "yield" means the ratio of the moles of maleic anhydride obtained to the moles of nonaromatic hydrocarbon feedstock introduced into the reaction zone multiplied by 100, the term expressed as mole %. The term "selectivity" means the ratio of moles of maleic anhydride obtained to the moles of hydrocarbons feed stock reacted or converted multiplied by 100, the term expressed as mole %. The term "conversion" means the ratio of moles of hydrocarbon feed stock reacted to the moles of hydrocarbon feed stock introduced into the reaction zone multiplied by 100, the term expressed as mole %. The term "space velocity" or "gas hourly space velocity" or "GHSV" means the hourly volume of gaseous feed expressed in cubic centimeters (cc) at 20° C. and atmospheric pressure, divided by the catalyst bulk volume, expressed in cubic centimeters, the term expressed as cc/cc/hour or $hr^{-1}$.

Catalysts suitable for use in the instant invention are those known to the art, and in general, are materials capable of catalyzing the vapor phase partial oxidation of nonaromatic hydrocarbons to maleic anhydride under oxidation conditions. Examples of useful catalysts are those described in the references previously noted in the "Description of the Prior Art", it being understood, however, that the same are not to be construed as limiting but instead are for purposes of illustration and guidance in the practice of the instant invention. Among such catalysts, those preferred for use according to the instant invention are the iron/lithium promoted phosphorus-vanadium mixed oxide oxidation catalysts described in U.S. Pat. No. 4,632,915. This reference and the references noted in the "Description of the Prior Art" are herein incorporated by reference.

In operation of the process of the instant invention, the oxidation catalyst is diluted with an inert solid material in an amount sufficient to form a catalyst-inert solid material composition effective to stabilize the maleic anhydride yields such that average yield decay is less than 0.30%, preferably less than 0.25%, of the established initial maleic anhydride yield per month over an extended period of sustained operations and charged to the reaction zone. The resultant diluted catalyst pack is graded in dilution such that maximum dilution occurs in the region of the catalyst pack in which the hottest point (highest temperature) of the reaction zone, (commonly referred to as "hot spot") is located. Typically, the hot spot is located at the point at which the oxidation rate for the hydrocarbon is maximum and the reaction is most exothermic and occurs within that region of the reaction zone which extends over the initial 50% of the length of the catalyst pack, proceeding from the feed inlet end to the exit end of the reaction zone. Maximum dilution at the typical hot spot location, therefore, tends to reduce the reaction rate and heat generation at such location.

Suitable configurations for the diluted catalyst pack are not narrowly critical and will vary depending upon a variety of factors such as overall catalyst pack length, production rate, composition of the active catalyst, and reaction conditions, and can be determined by routine experimentation by those skilled in the art in light of the disclosure provided herein. Nonlimiting examples include (a) a configuration in which the diluted catalyst pack is graded in dilution such that dilution decreases over at least a portion of the catalyst pack length from maximum dilution nearest the feed inlet end to minimum dilution nearest the exit end and (b) a configuration in which a first portion of the catalyst pack, proceeding from the feed inlet end to the exit end, has minimum dilution and the remainder of the catalyst pack is graded from maximum dilution nearest the feed inlet end to minimum dilution nearest the exit end. In the latter configuration, the initial minimum dilution zone or stage of the catalyst pack preferably is relatively short and advantageously can serve as a preheating zone for the hydrocarbon-molecular oxygen-containing gas feed stream.

It is contemplated in the instant invention that the catalyst pack, proceeding from the feed inlet end to the exit end, can be graded continuously and/or in stages. Ideally, dilution decreases continuously from maximum dilution to minimum dilution. However, from a practical standpoint, it is more convenient to provide two or more dilution zones or stages along the graded portion of the catalyst back length. Preferably, the number of stages range from two to about 10, with about three to about eight being most preferred.

Referring to the catalyst pack configuration in which the diluted catalyst pack is graded in dilution such that dilution decreases over at least a portion of the catalyst pack length from maximum dilution nearest the feed inlet end to minimum dilution nearest the exit end, in a preferred embodiment, the catalyst pack is divided into three dilution stages or zones—maximum, intermediate, and minimum—with the maximum dilution stage being located nearest the feed inlet end of the catalyst pack and the minimum dilution stage nearest the exit end. If the entire length of the catalyst pack is divided into 100 equal parts, beginning at the feed inlet end and ending at the exit end, the maximum dilution stage (Stage 1) of the catalyst pack advantageously extends from zero (0) parts per length (ppl) to about 20 ppl of the catalyst pack, with the catalyst pack being diluted with inert solid material in an amount sufficient to provide a catalyst-inert solid material composition having a catalyst/inert solid material weight ratio of from about 50/50 to about 75/25. The intermediate dilution stage (Stage 2) of the catalyst pack extends from about 20 ppl to about 40 ppl of the catalyst pack, with the catalyst pack being diluted with inert solid materials in an amount sufficient to provide a catalyst-inert solid material composition having a catalyst/inert solid material weight ratio of from about 76/24 to about 85/15. The remaining length of the catalyst pack is comprised of a minimum dilution stage (Stage 3). The minimum dilution stage extends from about 40 ppl to 100 ppl of the catalyst pack length. In such stage, the catalyst/inert solid material weight ratio ranges from about 86/14 to about 100/0.

In summary, in such configuration having the preferred three dilution stages of the catalyst pack, the distribution or gradations may be stated as follows:

| Stage | Dilution | Location of Stage, ppl | Catalyst/Inert Solid Material wt. ratio |
|---|---|---|---|
| 1 | Maximum | 0–20 | 50/50–75/25 |
| 2 | Intermediate | 20–40 | 76/24–85/15 |
| 3 | Minimum | 40–100 | 86/14–100/0 |

Referring to the catalyst pack configuration in which a first portion of the catalyst pack, proceeding from the feed inlet end to the exit end, has minimum dilution and the remainder of the catalyst pack is graded from maximum dilution nearest the feed inlet end to minimum dilution nearest the exit end, in a preferred embodiment, the catalyst is divided into three dilution stages—Stage 1 (minimum dilution stage), Stage 2 (maximum dilution stage), and Stage 3 (minimum dilution stage)—with Stage 1 being located nearest the feed inlet end of the catalyst pack, Stage 3 nearest the exit end, and Stage 2 between Stages 1 and 3. Dividing the entire length of the catalyst pack into 100 equal parts, beginning at the feed inlet end and ending at the exit end as previously described, Stage 1 of the catalyst pack advantageously extends from zero (0) ppl to about 18 ppl of the catalyst pack. In Stage 1, the catalyst pack preferably is diluted with inert solid material in an amount sufficient to provide a catalyst-inert solid material composition having a catalyst/inert solid material weight ratio of from about 86/14 to about 100/0. Stage 2 of the catalyst pack extends from about 18 ppl to about 45 ppl of the catalyst pack, with the catalyst pack being diluted with inert solid materials in an amount sufficient to provide a catalyst-inert solid material composition having a catalyst/inert solid material weight ratio of from about 51/49 to about 85/15. The remaining portion of the catalyst pack (Stage 3) extends from about 45 ppl to 100 ppl of the catalyst pack length. In such stage, the catalyst/inert solid material weight ratio ranges from about 86/14 to about 100/0.

In summary, in such configuration having the preferred three dilution stages of the catalyst pack, the distribution or gradations may be stated as follows:

| Stage | Dilution | Location of Stage, ppl | Catalyst/Inert Solid Material wt. ratio |
|---|---|---|---|
| 1 | Minimum | 0–18 | 86/14–100/0 |
| 2 | Maximum | 18–45 | 51/49–85/15 |
| 3 | Minimum | 45–100 | 86/14–100/0 |

Any suitable means for providing the desired dilution gradient is contemplated according to the instant invention. Most simply, structured oxidation catalyst—pellets or tablets, for example—is employed, with the desired dilution gradation being accomplished by blending of structured catalyst with an inert solid material. Suitable inert solid material diluents include materials which do not adversely affect catalyst performance in the oxidation reaction and which are at least generally similar to the structured catalyst in terms of size and shape so that a substantially uniform flow of gas through the catalyst pack is insured. Specific, nonlimiting examples of suitable inert solid materials (diluents) include alumina, silica, alumina-silica, and silicon carbide, and mixtures thereof, with alumina and alumina-silica generally being preferred. A continuous dilution gradient can be provided by feeding structured catalyst and inert solid material to the reaction zone using separate variable speed feeders. Staged gradients can be provided by batchwise blending of structured catalyst and inert solid material in appropriate amounts.

A related method of achieving the desired dilution gradient is to employ a supported catalyst in which the proportion of active catalyst increases from the maximum to minimum dilution stages. Nonlimiting representative supports include alumina, silica, silica gel, silica carbide, ceramic doughnuts, magnesia, titania, and titania-silica.

The diluted catalysts employed in accordance with the instant process are useful in a variety of reactors to convert nonaromatic hydrocarbons to maleic anhydride. A typically satisfactory reactor is a heat transfer medium-cooled fixed bed tube-type reactor. The details of operation of such reactors are well known to those skilled in the art. The tubes of such reactors can be constructed of iron, stainless steel, carbon steel, nickel, glass, such as Vycor, and the like and can vary in diameter from about 0.635 cm (0.25 in.) to about 3.81 cm (1.50 in.) and the length can vary from about 15.24 cm (6 in.) to about 609.60 cm (20 ft). The oxidation reaction is highly exothermic and once reaction is underlay, in order to maintain the desired reaction zone temperature, a heat transfer medium is necessary to conduct heat away from the reaction zone. Suitable heat transfer media are well known to those skilled in the art and, in general, are materials that remain in the liquid state at process temperatures and have a relatively high thermal conductivity. Examples of useful media include various heat transfer oils, molten sulfur, mercury, molten lead, and salts such as nitrates and nitrites of alkali metals, the salts being preferred due to their high boiling points. A particularly preferred heat transfer medium is a eutectic mixture of potassium nitrate, sodium nitrate and sodium nitrite which not only has a desirably high boiling point, but also, a sufficiently low freezing point that it remains in a liquid state even during periods of reaction zone shutdown. An additional method of temperature control is to use a metal block reactor whereby the metal surrounding the reaction zone acts as a temperature regulating body or by conventional heat exchangers.

In general, operations in accordance with the instant invention involve charging a mixture of nonaromatic hydrocarbon having at least four carbon atoms in a straight chain and a molecular oxygen-containing gas (including molecular oxygen), such as air to a heat transfer medium-cooled reaction zone packed with a diluted catalyst to contact the catalyst with the hydrocarbon-molecular oxygen-containing gas mixture at a temperature between about 300° C. and about 600° C. at concentrations of from about 1 mole % to about 10 mole % hydrocarbon at a gas hourly space velocity (GHSV), or simply space velocity, up to about 4,000 $hr^{-1}$ to produce maleic anhydride. However, the yield of maleic anhydride under such circumstances may be initially low; and if this in the case, the catalyst, as will occur to those skilled in the art, can be "conditioned" by contacting the diluted catalyst pack with low concentrations of hydrocarbon and molecular oxygen-containing gas at low space velocities for a period of time before production operations begin to establish an initial or baseline maleic anhydride yield.

In a typical operation, the hydrocarbon is admixed with the molecular oxygen-containing gas, preferably air, at a concentration of about 1 mole % to about 10 mole % hydrocarbon, preferably about 2 mole % to about 5 mole %, and contacted with the diluted catalyst at a space velocity of about 100 $hr^{-1}$ to about 4,000 $hr^{-1}$ at a temperature between about 300° C. and about 600° C., preferably from about 1,000 $hr^{-1}$ to about 3,000 $hr^{-1}$ and from about 325° C. to about 500° C. to provide a single-pass conversion of at least about 70%, preferably at least about 75% to about 85%, most preferably at least about 78% to about 82%, of the hydrocarbon fed to the reaction zone and an excellent yield of, and selectivity to, maleic anhydride.

Pressure is not critical in the reaction to convert nonaromatic hydrocarbons to maleic anhydride in accordance with the instant invention. The reaction may be conducted at atmospheric, superatmospheric, or subatmospheric pressure. It generally will be preferred, however, for practical reasons, to conduct the reaction at or near atmospheric pressure. Typically, pressures of from about $1.013 \times 10^2$ kilopascals-gauge (kPa-g, 14.7 psig, 1 atm) to about $3.45 \times 10^2$ kPa-g (50.0 psig), most preferably from about $1.24 \times 10^2$ kPa-g (18.0 psig) to about $2.068 \times 10^2$ kPa-g (30.0 psig), may be conveniently employed.

Maleic anhydride produced in accordance with the process of the instant invention can be recovered by any means known to those skilled in the art. For example, maleic anhydride can be recovered by direct condensation or by absorption in suitable media with subsequent separation and purification of the anhydride.

A large number of nonaromatic hydrocarbons having from four to 10 carbon atoms can be converted to maleic anhydride in the process of the instant invention. It is only necessary that the hydrocarbon contain not less than four carbon atoms in a straight chain. As an example, the saturated hydrocarbons n-butane is satisfactory, but isobutane (2-methyl propane) is not satisfactory for conversion to maleic anhydride although its presence is not harmful. In addition to n-butane, other suitable saturated hydrocarbons include the pentanes, the hexanes, the heptanes, the octanes, the nonanes, the decanes, and mixtures of any of these, with or without n-butane, so long as a hydrocarbon chain having at least four carbon atoms in a straight chain is present in the saturated hydrocarbon molecule.

Unsaturated hydrocarbons are also suitable for conversion to maleic anhydride in accordance with the process of the instant invention. Suitable unsaturated hydrocarbons include the butenes (1-butene and 2-butene), 1,3-butadiene, the pentenes, the hexenes, the heptenes, the octanes, the nonenes, the decenes and mixtures of any of these, again, so long as the requisite hydrocarbon chain having at least four carbon atoms in a straight chain is present in the molecule.

Cyclic compounds such as cyclopentane and cyclopentene are also satisfactory feed materials for conversion to maleic anhydride.

Of the aforementioned feedstocks, n-butane is the preferred saturated hydrocarbon and the butenes are the preferred unsaturated hydrocarbons, with n-butane being most preferred of all feedstocks.

It will be noted that the aforementioned feedstocks need not necessarily be pure substances, but can be technical grade hydrocarbons.

The principal product from the oxidation of the aforementioned suitable feed materials is maleic anhydride, although small amounts of citraconic anhydride (methyl maleic anhydride) may also be produced when the feedstock is a hydrocarbon containing more than 4 carbon atoms.

The following specific examples illustrating the best currently-known method of practicing this invention are described in detail in order to facilitate a clear understanding of the invention. It should be understood, however, that the detailed expositions of the application of the invention, while indicating preferred embodiments, are given by way of illustration only and are not to be construed as limiting the invention since various changes and modifications within the spirit of the invention will become apparent to those skilled in the art from this detailed description.

EXAMPLE 1 (Comparative)

The catalyst employed was an iron/lithiumpromoted phosphorus-vanadium catalyst represented by the formula $P_{1.20}V_{1.00}Fe_{0.0016}Li_{0.0030}O_x$ and prepared substantially as described in Example 1 of U.S. Pat. No. 4,632,915, except that a reactor having a charge zone of 2.12 cm (0.834 in.) inside diameter x 589.28 cm (19.33 ft, 232.0 in.) was employed. The catalyst was performance tested substantially as described in Example 1 of U.S. Pat. No. 4,632,915 in the calcination reactor at 1150 hr$^{-1}$ space velocity and 2.4 mole % n-butane-in-air. The parameter's and results are tabulated in Table 1.

EXAMPLE 2

The catalyst and reactor described in Example 1 were employed, except that the catalyst in the reactor was graded by blending weighed amounts of catalyst and alumina-silica spheres having a weight % composition of 86.1% α-alumina ($Al_2O_3$) and 11.8% silica ($SiO_2$) [and trace amounts of sodium oxide ($Na_2O$), iron (III) oxide ($Fe_2O_3$), titania ($TiO_2$) calcium oxide (CaO), magnesia (MgO), potassium oxide (KzO)] and a BET surface area of 0 05 m$^2$/g and identified by the Norton Company product number ("SA-5205") of the same general size and shape as the catalyst tablets. Bulk densities of the catalyst an aluminasilica were identical [0.83 g/cm$^3$ (52 lb/ft$^3$)]. The catalyst pack was graded along its 589.28 cm length from maximum dilution at the feed inlet end to minimum dilution nearest the exit end according to the following profile:

| Stage | Dilution | Length, cm | Catalyst/<br>Alumina-Silica<br>wt. ratio |
|---|---|---|---|
| 1 | Maximum | 0–101.6 | 70/30 |
| 2 | Intermediate | 101.6–203.2 | 80/20 |
| 3 | Minimum | 203.2–589.28 | 100/0 |

The diluted catalyst pack was performance tested as described in Example 1. The parameters and results are tabulated in Table 2.

TABLE 2

| Example | n-Butane mole % | Space Velocity hr$^{-1}$ | Temperature, °C. Bath | Temperature, °C. Reaction | Conversion mole % | Selectivity mole % | Yield mole % |
|---|---|---|---|---|---|---|---|
| 2 (Initial) | 2.4 | 1150 | 426 | 463 | 82.0 | 67.1 | 55.0 |
| 2 (Final)[1] | 2.4 | 1220 | 435 | 463 | 82.0 | 65.9 | 54.0 |

[1]After eight months of sustained operations. The maleic anhydride yield decay was 1.82% of the initial maleic anhydride yield, giving an average maleic anhydride yield decay of 0.23% per month.

Thus, it is apparent that there has been provided, in accordance with the instant invention, a process that fully satisfies the objects and advantages set forth hereinabove. While the invention has been described with respect to various specific examples and embodiments thereof, it is understood that the invention is not limited thereto and that many alternatives, modifications, and variations will be apparent to those skilled in the art in light of the foregoing description. Accordingly, it is intended to embrace all such alternatives, modifications, and variations that fall within the spirit and broad scope of the invention.

What is claimed is:

1. In a process for the production of maleic anhydride by the catalytic vapor phase partial oxidation of nonaromatic hydrocarbons having at least four carbon atoms in a straight chain with molecular oxygen or a molecular oxygen-containing gas in the presence of a phosphorus-vanadium mixed oxide oxidation catalyst having a phosphorus/vanadium atom ratio of about 0.5 to about 2.0, said catalyst containing a promoter compo-

TABLE 1

| Example | n-Butane mole % | Space Velocity hr$^{-1}$ | Temperature, °C. Bath | Temperature, °C. Reaction | Conversion mole % | Selectivity mole % | Yield mole % |
|---|---|---|---|---|---|---|---|
| 1 (Initial) | 2.4 | 1150 | 421 | 452 | 80.0 | 66.3 | 53.0 |
| 1 (Final)[1] | 2.4 | 1150 | 441 | 481 | 81.0 | 61.7 | 50.0 |

[1]After eight months of sustained operations. The maleic anhydride yield decay was 5.66% of the initial maleic anhydride yield, giving an average maleic anhydride yield decay of 0.71% per month.

nent comprising each of iron and lithium the oxidation being conducted in a heat transfer medium-cooled fixed bed tube-type reaction zone packed with the catalyst under conditions sufficient to provide a single pass conversion of at least 70% of the hydrocarbon fed to the reaction zone and establish an initial maleic anhydride yield, the improvement comprising diluting the catalyst with an inert solid material in an amount sufficient to form a catalyst-inert solid material composition ffective to stabilize the maleic anhydride yield such that average yield decay is less than 0.30% of the established initial maleic anhydride yield per month over an extended period of sustained operations.

2. The process improvement of claim 1 wherein the catalyst has a phosphorus/vanadium atom ratio of from about 0.95 to about 1.2.

3. The process improvement of claim 1 wherein the nonaromatic hydrocarbon is a saturated hydrocarbon.

4. The process improvement of claim 5 wherein the saturated hydrocarbon is n-butane.

5. The process improvement of claim 1 wherein the molecular oxygen-containing gas is air.

6. The process improvement of claim 5 wherein the nonaromatic hydrocarbon-in-air concentration is from about 1 mole % to about 10 mole %.

7. The process improvement of claim 6 wherein the nonaromatic hydrocarbon-in-air concentration is from about 2 mole % to about 5 mole %.

8. The process improvement of claim 1 wherein the reaction is conducted at a temperature of from about 300° C. to about 600° C. a pressure of from about $1.013 \times 10^2$ kPa-g to about $3.45 \times 10^2$ kPa-g, and a space velocity of from about 100 hr$^{-1}$ to about 4,000 hr$^{-1}$.

9. The process improvement of claim 8 wherein the temperature is from about 325° C. to about 500° C., the pressure is from about $1.24 \times 10^2$ kPa-g to about $2.068 \times 10^2$ kPa-g, and the space velocity is about 1000 hr$^{-1}$ to about 3000 hr$^{-}$.

10. The process improvement of claim 1 wherein the conversion of the nonaromatic hydrocarbon fed to the reaction zone is at least about 75% to about 85%.

11. The process improvement of claim 10 wherein the conversion of the nonaromatic hydrocarbon fed to the reaction zone is at least about 78% to about 82%.

12. The process improvement of claim 1 wherein the established initial maleic anhydride yield is at least 50 mole %.

13. The process improvement of claim 1 wherein the inert solid material is selected from the group consisting of alumina, silica, alumina-silica, and silicon carbide, and mixtures thereof.

14. The process improvement of claim 14 wherein the inert solid material is alumina-silica.

15. The process improvement of claim 1 wherein the diluted catalyst is graded in dilution such that dilution decreases over at least a portion of the catalyst pack length from maximum dilution nearest the feed inlet end to minimum dilution nearest the exit end.

16. The process improvement of claim 15 wherein the entire length of the catalyst pack is graded from maximum dilution nearest the feed inlet end to minimum dilution nearest the exit end.

17. The process improvement of claim 15 wherein the catalyst pack is graded continuously from maximum dilution nearest the feed inlet end to minimum dilution nearest the exit end.

18. The process improvement of claim 15 wherein the catalyst pack is graded in dilution stages from maximum dilution nearest the feed inlet end to minimum dilution nearest the exit end.

19. The process improvement of claim 18 wherein the number of dilution stages in the catalyst pack range from about two to about 10.

20. The process improvement of claim 19 wherein the number of dilution stages in the catalyst pack range from about three to about eight.

21. The process improvement of claim 20 wherein the number of dilution stages in the catalyst pack is three.

22. The process improvement of claim 21 wherein the three dilution stages along the length of the catalyst pack, proceeding from the feed inlet end to the exit end, are (a) a maximum dilution stage, (b) an intermediate dilution stage, and (c) a minimum dilution stage.

23. The process improvement of claim 22 wherein (a) the maximum dilution stage extends from zero parts per length to about 20 parts per length of the catalyst pack, (b) the intermediate dilution stage extends from about 20 parts per length to about 40 parts per length of the catalyst pack, and (c) the minimum dilution stage extends from about 40 parts per length to 100 parts per length of the catalyst pack.

24. The process improvement of claim 23 wherein (a) the maximum dilution stage has a catalyst/inert solid material weight ratio of from about 50/50 to about 75/25, (b) the intermediate dilution stage has a catalyst/inert solid material weight ratio of from about 76/24 to about 85/15, and (c) the minimum dilution stage has a catalyst/inert weight ratio from about 86/14 to about 100/0.

25. The process improvement of claim 24 wherein (a) the maximum dilution stage has a catalyst/inert solid material weight ratio of about 70/30, (b) the intermediate dilution stage has a catalyst/inert solid material weight ratio of from about 80/20, and (c) the minimum dilution stage has a catalyst/inert solid material weight ratio of about 100/0.

26. The process improvement of claim 15 wherein a first portion of the catalyst pack, proceeding from the feed inlet end to the exit end, has minimum dilution and the remainder of the catalyst pack is graded from maximum dilution nearest the feed inlet end to minimum dilution nearest the exit end.

27. The process improvement of claim 26 wherein the catalyst pack is graded in dilution stages along its entire length.

28. The process improvement of claim 27 wherein the number of dilution stages in the catalyst pack is three.

29. The process improvement of claim 28 wherein the three dilution stages along the length of the catalyst, proceeding from the feed inlet end to the exit end, are (a) a first dilution stage having minimum dilution, (b) a second dilution stage having maximum dilution, and (c) a third dilution stage having minimum dilution.

30. The process improvement of claim 28 wherein (a) the first dilution stage of the catalyst pack extends from zero parts per length to about 18 parts per length of the catalyst pack, (b) the second dilution stage of the catalyst pack extends from about 18 parts per length to about 45 parts per length of the catalyst pack, and (c) the third dilution stage of the catalyst pack extends from about 45 parts per length to 100 parts per length of the catalyst pack.

31. The process improvement of claim 29 wherein (a) the first dilution stage has a catalyst/inert solid material weight ratio of from about 86/14 to about 100/0, (b) the second dilution stage has a catalyst/inert solid material weight ratio of from about 51/49 to about 85/15, and (c) the third dilution stage has a catalyst/inert solid material weight ratio of from about 86/14 to about 100/0.

32. The process improvement of claim 31 wherein (a) the first dilution stage has a catalyst/inert solid material weight ratio of about 100/0, (b) the second dilution stage has a catalyst/inert solid material weight ratio of about 85/15, and (c) the third dilution stage has a catalyst/inert solid material weight ratio of about 100/0.

33. The process improvement of claim 1 wherein the extended period of sustained operations is at least six (6) months.

34. The process improvement of claim 1 wherein the average yield decay is less than 0.25% per month.

* * * * *

UNITED STATES PATENT AND TRADEMARK OFFICE
CERTIFICATE OF CORRECTION

PATENT NO. : 4,855,459

DATED : August 8, 1989

INVENTOR(S) : Michael J. Mummey

It is certified that error appears in the above-identified patent and that said Letters Patent is hereby corrected as shown below:

In Column 1, line 52, delete "phosphorusvanadium" and insert therefor --phosphorus-vanadium--.

In Column 5, line 58, insert "," after the number "2.0".

In Column 7, line 54, delete "back" and insert therefor --pack--.

In Column 9, line 51, delete "underlay" and insert therefor --underway--.

In Column 11, line 8, delete "octanes" and insert therefor --octenes--.

In Column 11, line 50, delete "iron/lithiumpromoted" and insert therefor --iron/lithium-promoted--.

In Column 12, line 14, delete "aluminasilica" and insert therefor --alumina-silica--.

In Column 13, line 9, delete "ffective" and insert therefor --effective--.

UNITED STATES PATENT AND TRADEMARK OFFICE
CERTIFICATE OF CORRECTION

PATENT NO. : 4,855,459

DATED : August 8, 1989

INVENTOR(S) : Michael J. Mummey

It is certified that error appears in the above-identified patent and that said Letters Patent is hereby corrected as shown below:

In Column 13, line 31, insert "," after "600°C."

Signed and Sealed this

Second Day of October, 1990

Attest:

HARRY F. MANBECK, JR.

Attesting Officer      Commissioner of Patents and Trademarks